United States Patent [19]

D'Amico

[11] 4,282,029

[45] Aug. 4, 1981

[54] N-(PYRIDYLMETHYL)-2-OXOBENZO-THIAZOLINE DERIVATIVES AND THEIR USE AS PLANT GROWTH REGULANTS

[75] Inventor: John J. D'Amico, Olivette, Mo.

[73] Assignee: Monsanto Company, St. Louis, Mo.

[21] Appl. No.: 117,403

[22] Filed: Jan. 31, 1980

[51] Int. Cl.³ .................... C07D 513/04; A01N 43/86
[52] U.S. Cl. .......................................... 71/90; 546/270
[58] Field of Search ............................ 546/270; 71/90

[56] References Cited

U.S. PATENT DOCUMENTS

| 3,538,109 | 11/1970 | Halasa ................................. 546/270 |
| 4,075,216 | 2/1978 | D'Amico ............................ 546/270 |
| 4,166,910 | 9/1979 | Wade et al. .......................... 546/270 |

Primary Examiner—Alan L. Rotman
Attorney, Agent, or Firm—Patricia A. Coburn; Donald W. Peterson

[57] ABSTRACT

The present invention relates to N-(pyridylmethyl)-2-oxobenzothiazoline and N-(pyridylmethyl)-2-oxobenzoxazoline compounds of the formula

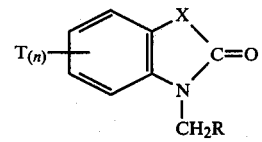

wherein:
T is hydrogen, alkyl containing 1 to 5 carbon atoms, halo, —$CF_3$, —CN or —$NO_2$
n is zero, 1 or 2; X is oxygen or sulfur; R is equal to

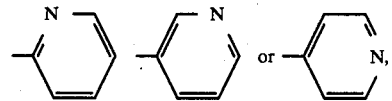

their use in a method of regulating leguminous plant growth as well as compositions containing the novel compounds as the active ingredient.

21 Claims, No Drawings

N-(PYRIDYLMETHYL)-2-OXOBENZOTHIAZOLINE DERIVATIVES AND THEIR USE AS PLANT GROWTH REGULANTS

SUMMARY OF THE INVENTION

This invention relates to new N-pyridylmethyl-2-oxobenzothiazoline and -2-oxobenzoxazoline derivatives and to their use as leguminous plant growth regulants as well as to plant growth regulant compositions.

DESCRIPTION OF THE INVENTION

The invention relates to a new class of chemical compounds and their use as plant growth regulants. More specifically, the invention relates to novel N-pyridylmethyl-2-oxobenzothiazoline and -2-oxobenzoxazoline derivatives useful in regulating the growth of leguminous plants.

N-pyridylmethyl-2-oxobenzothiazolines and -2-oxobenzoxazolines useful in accordance with this invention are represented by the formula

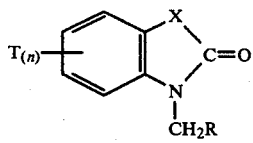

wherein:

T is hydrogen, alkyl containing 1 to 5 carbon atoms alkyl, halo, —CF$_3$, —CN or —NO$_2$, n is zero, 1 or 2; x is oxygen or sulfur;

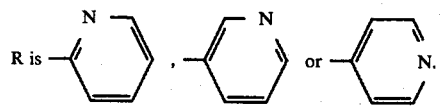

In the description of the novel compounds of this invention which are useful as plant growth regulants, the following embodiments are intended for the various groups.

Alkyl includes those members including straight and branched chain, as for example, methyl, ethyl, n-propyl, isopropyl, n-butyl, sec-butyl, tert-butyl, n-pentyl, isopentyl, and the like.

The term "halo" or "halogen", when used herein, refers to chlorine, bromine, fluorine or iodine atoms.

The compounds of this invention are prepared according to the following reaction:

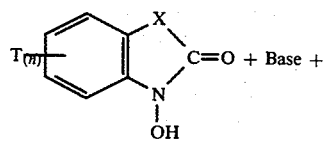

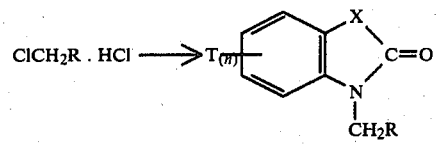

where T, n, X and R are as previously defined.

More specifically, the compounds of the present invention are prepared by dissolving an appropriate 2-hydroxybenzothiazole or 2-hydroxybenzoxazole, starting material with an excess of base, as for example, NaOH, KOH, etc. in a water-miscible solvent, e.g. water and/or acetone. To the solution of starting material is added 2-, 3- or 4-picolylchloride hydrochloride and the mixture stirred for 24 to 48 hours to complete reaction. Thereafter, the reaction product is separated and collected using conventional techniques well known in the art.

The reaction described above is carried out in the presence of a water-miscible solvent, as for example, water, acetone, methanol, and the like and in the presence of strong base, e.g. NaOH or KOH. The base, preferable being present in excess.

The starting 2-hydroxybenzothiazole and/or 2-hydroxybenzoxazole compounds and the picolyl chloride hydrochloride are preferably used in stoichiometric proportions although greater than stoichiometric proportions may be used.

Conditions of temperature and pressure for effecting the synthesis of the compounds of the present invention are, in general, not critical. The reaction proceeds smoothly at atmospheric pressures and at room temperature. However, pressures above or below atmospheric may be employed and temperatures within the range of from about room temperature to at or near reflux may be employed, preferably the temperature of the reaction is maintained at or near reflux.

The separation of reaction product from the reaction mixture is carried out utilizing conventional methods well known in the art, as for example, filtration.

The purification of the reaction products can, if desired, be effected by recrystallization from organic solvents, especially from alcohols such as methanol or ethanol.

The following example describes in detail the preparation of the compounds of this invention. This example is presented merely as illustration, since it will be apparent to those skilled in the art that many modifications both of materials and methods may be practiced within the spirit and scope of the present disclosure.

EXAMPLE 1

To a stirred solution containing 0.2 mole of the appropriate 2-hydroxybenzothiazole or 2-hydroxybenzoxazole, 26.4 g (0.4 mole) of 85% potassium hydroxide, 150 ml of water and 150 ml of acetone, 34.9 g (0.2 mole) was added 2-, 3- or 4-picolylchloride hydrochloride in one portion, with continued stirring. The stirred reaction mixture was heated at reflux for 24 hours. After cooling to 5° C., 800 g of ice water was added and stirring continued at 0°–10° C. for one hour. The solid was collected by filtration, washed with H$_2$O until neutral to litmus and air-dried at 25°–30° C. The data are summarized in Table I.

TABLE I $$T_{(n)}\!\!-\!\!\underset{\underset{OH}{N}}{\overset{X}{\bigcirc}}\!\!C\!=\!O + 2KOH + ClCH_2R \cdot HCl \longrightarrow T_{(n)}\!\!-\!\!\underset{\underset{CH_2R}{N}}{\overset{X}{\bigcirc}}\!\!C\!=\!O$$

| Compound No. | T | m | X | R | M.P. °C. | % Yield | %C Calc'd | %C Found | %H Calc'd | %H Found | %N Calc'd | %N Found | %S Calc'd | %S Found |
|---|---|---|---|---|---|---|---|---|---|---|---|---|---|---|
| 1 | H | 1 | S | 2-pyridyl | 102-3[a] | 90 | 64.44 | 64.36 | 4.16 | 4.18 | 11.56 | 11.56 | 13.23 | 13.25 |
| 2 | 6-OC$_2$H$_5$ | 1 | S | 2-pyridyl | 89-90[b] | 84 | 62.92 | 62.88 | 4.93 | 4.95 | 9.78 | 9.79 | 11.20 | 11.13 |
| 3 | 6-Br | 1 | S | 2-pyridyl | 114-5[a] | 84 | 48.61 | 48.79 | 2.82 | 2.57 | 8.72 | 8.76 | 9.98 | 10.05 |
| 4 | H | 1 | S | 3-pyridyl | 93-5[c] | 66 | 64.44 | 64.57 | 4.16 | 4.23 | 11.56 | 11.57 | 13.23 | 13.17 |
| 5 | 5-Cl | 1 | S | 3-pyridyl | 105-6[a] | 92 | 56.42 | 56.50 | 3.28 | 3.33 | 10.12 | 10.09 | 11.59 | 11.55 |
| 6 | H | 1 | O | 3-pyridyl | 138-40[b] | 53 | 69.02 | 68.94 | 4.46 | 4.48 | 12.38 | 12.34 | — | — |
| 7 | 6-NO$_2$ | 1 | S | 2-pyridyl | 158-160[d] | 23 | 54.35 | 54.32 | 3.16 | 3.11 | 14.63 | 14.84 | 11.16 | 10.90 |
| 8 | H | 1 | O | 2-pyridyl | 108-9[b] | 59 | 69.02 | 68.97 | 4.46 | 4.46 | 12.38 | 12.35 | — | — |
| 9 | 6-Br | 1 | S | 3-pyridyl | 167-8[b] | 28 | 48.61 | 48.70 | 2.82 | 2.85 | 8.72 | 8.71 | 9.98 | 9.98 |
| 10 | H | 1 | O | 4-pyridyl | 140-2[b] | 22 | 69.02 | 68.92 | 4.46 | 4.50 | 12.38 | 12.34 | — | — |
| 11 | H | 1 | S | 4-pyridyl | 115-6[c] | 91 | 64.44 | 64.47 | 4.16 | 4.20 | 11.56 | 11.56 | 13.23 | 13.23 |

[a] Recrystallization from methyl alcohol.
[b] Recrystallization from isopropyl alcohol.
[c] Recrystallization from isopropyl alcohol - Heptane (1:3).
[d] Recrystallization from isopropyl alcohol - Ethyl Acetate (2:1).

As has been noted, the compounds of the present invention are active as leguminous plant growth regulants. The term "active ingredient" is used herein to describe the novel N-pyridylmethyl-2-oxobenzothiazolines and -2-oxobenzoxazolines of the formula previously described. These compounds have been found to produce a variety of plant growth regulatory responses when applied to leguminous crop plants, for example, soybean (Glycine max). The terms "plant growth regulant effect", "plant growth regulation" or words to that effect, are used in this specification and in the claims to mean the causation by the chemicals of the present invention, of a variety of plant responses which achieve a promotion, inhibition or modification of any plant physiological or morphological process. It should additionally be recognized that various plant responses may also result from a combination or sequence of both physiological and morphological factors.

The plant growth regulant effects which may be produced in leguminous plants using the method of the present invention are probably most readily observable as changes in the size, shape, color or texture of the treated plant or any of its parts. The above changes may be characterized as an acceleration or retardation of plant growth, leaf or canopy alteration, increased branching, tillering, terminal inhibition, axillary bud development or inhibition, defoliation and the like.

Although many of the above modifications are per se desirable, it is most often the ultimate effect of such modifications on the economic factor that is of primary significance. For example, reducing the physical size of each plant in a field permits the growing of more plants per unit area and leads to more efficient use of crop land. Many plants of reduced stature are more tolerant of drought and cold temperatures and are more resistant to pest infestations and to lodging. Reduction in the maturation rate on portions of a crop permits an extended harvest period at peak yield and more efficient use of subsequent crop processing equipment. Suppression of vegetative growth at the appropriate stage of the plant's development may result in increased energy available for utilization in reproductive development so that, for example, more fruit or larger fruit is formed.

Increased plant dry matter accumulation is a valuable plant growth regulant response which can occur in conjunction with morphological changes or can be the sole plant growth response detected. Increased dry matter accumulation is the physically measurable manifestation of increased plant photosynthetic activity. Most plants capture no more than 1 to 3 percent of the solar energy they receive. Present knowledge suggests that it is theoretically possible to increase this rate to approximately twelve percent. Enhancement of photosythesis at the appropriate stage of the plant's growth and development may enable the plant to fix more carbon dioxide resulting in the production of increased amounts of carbohydrate, amino acids, etc., which could be available for utilization in the plant's reproductive activities, leading to increased crop yields.

Decreased dry matter accumulation may indicate a reduction in photosynthesis activity or also a reduction of some other critical metabolic pathway which ultimately affects the total growth of the plant, as for example, amino acid synthesis.

It is to be understood that the regulation of desirable crop plants in accordance with the instant invention does not include the total inhibition or the killing of such plants. It is contemplated here to employ only plant growth regulating amounts of such materials in order to modify the normal sequential development of the treated plant to agricultural maturity. The application of a plant regulating amount may be applied to plants in sequence at various stages of the plant's development to obtain various desirable responses. As may be expected, and as is apparent to those skilled in the art, such plant regulating amounts will vary, not only with the material selected, but also with the modifying effect desired, the species and its stages of development, the plant growth medium and whether a permanent or transitory effect is sought.

In accordance with this invention is has been found that desirable modification of leguminous crop plants is achieved by applying the above-described plant regulants to the "plant" or plant "habitat". The term "plant" is understood herein to include the seeds, emerging seedlings, roots, stems, leaves, flowers, fruits or other plant parts. The term "habitat" is understood herein to mean the environment of the plant such as the plant growing medium, e.g., the soil.

In the practice of the invention, the active ingredient can be used alone or in combination with a material referred to in the art as an adjuvant in either liquid or solid form. To prepare plant growth regulating compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well-known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing for example, spreaders, power dusters, boom and hand sprayers and spray dusters. The compositions can also be applied from airplanes as a dust or spray. Should the application of the plant growth composition to the plant growth medium be desired, this is accomplished by incorporating the compositions in the soil or other media in the area where modifications of the plant is desired.

Compositions of this invention generally contain from about 5 to 95 parts active ingredient, about 1 to 50 parts surface active agent and about 5 to 94 parts solvent, all parts being by weight based on the total weight of the composition.

In selecting the appropriate rate of application of the active ingredient, it will be recognized that precise rates will also be dependent upon the mode of application, such as soil incorporation, band application, pre-plant seed treatment and various other factors known to those skilled in the art. In foliar treatment for the regulation of plant growth, the active ingredients are applied in amounts of from about 0.05 to about 10 pounds per acre. Preferred are foliar applications of from 0.05 to 5 pounds of the active ingredient per acre. In application to the soil habitat of germinant seeds, emerging seedlings and established vegetation for the regulation of plant growth, the active ingredients are applied in amounts of from 0.1 to about 10 pounds per acre or more. The application to the soil of from 0.1 to about 5 pounds of active ingredient per acre is preferred. Foliar application to plants beginning to blossom are preferred over other types of applications.

In accordance with the practice of the invention, plant growth regulating compositions were formulated utilizing the 3-pyridylmethyl-2-oxobenzothiazoline or -2-oxobenzoxazoline derivatives of the present invention as the active ingredient. The plant growth regulating properties of the compounds of the invention are illustrated by the test set forth in Example 2.

EXAMPLE 2

A number of soybean plants, variety Williams, were grown from seeds in plastic pots in the greenhouse for a period of one week, at which time the plants were thinned to one plant per pot. When the second trifolate leaf (three weeks) was fully expanded, the plants were treated with a solution of the active ingredient in acetone and water containing Tween 20 surfactant. When the fifth trifoliate leaf (four to five weeks) was fully expanded, the treated plants were compared with the non-treated control plants and the observations recorded. Table II below, summarized the results and observations made in accordance with the above procedure when the compounds of the present invention were utilized as the active ingredient at several application rates.

The novel compounds described herein thiazoline exhibit unexpected properties when used to regulate the growth of leguminous crop plants, especially soybean (Glycine max).

TABLE II

| Compound No. | RATE Lbs/A | Kg/H | % Dry* Weight | Response |
|---|---|---|---|---|
| 11 | 0.1 | 0.14 | 89 | No response noted. |
|  | 0.5 | 0.56 | 85 | No response noted. |
|  | 2.5 | 2.80 | 63 | Leaf alteration, leaf alteration new growth, slight leaf burn. |
| 8 | 0.1 | 0.14 | 72 | No response noted. |
|  | 0.5 | 0.56 | 86 | No response noted. |
|  | 2.5 | 2.80 | 77 | Leaf distortion, leaf inhibition, leaf distortion new growth, leaf alteration new growth, slight leaf burn. |
|  | 0.1 | 0.14 | 75 | No response noted. |
| 6 | 0.5 | 0.56 | 89 | Leaf alteration, leaf inhibition, leaf alteration new growth, slight leaf burn, chlorosis. |
|  | 2.5 | 2.80 | 69 | Leaf alteration, leaf inhibition, leaf alteration new growth, moderate leaf burn, chlorosis. |
| 2 | 0.1 | 0.14 | 107 | No response noted. |
|  | 0.5 | 0.56 | 90 | No response noted. |
|  | 2.5 | 2.80 | 98 | Leaf alteration, leaf distortion, leaf alteration new growth, slight leaf burn. |
| 3 | 0.1 | 0.14 | 99 | No response noted. |
|  | 0.5 | 0.56 | 117 | No response noted. |
|  | 2.5 | 2.80 | 68 | Leaf alteration, leaf inhibition, leaf alteration new growth, slight leaf burn. |
| 3 | 0.1 | 0.14 | 98 | No response noted. |
|  | 0.5 | 0.56 | 81 | No response noted. |
|  | 2.5 | 2.80 | 85 | Leaf alteration new growth, slight leaf burn. |
| 1 | 0.1 | 0.14 | 97 | No response noted. |
|  | 0.5 | 0.56 | 101 | No response noted. |
|  | 2.5 | 2.80 | 66 | Leaf distortion, altered canopy, leaf inhibition, leaf distortion new growth, moderate leaf burn. |

*Calculated as percent of control

Although this invention has described with respect to specific modifications, the details thereof are not to be construed as limitations, for it will be apparent that various equivalents, changes, and modifications may be resorted to without departing from the spirit and scope thereof and it is understood that such equivalent embodiments are intended to be included herein.

I claim:

1. A compound of the formula wherein:
T is hydrogen, $C_{1-5}$ alkyl, halo, $-CF_3$, $-CN$ or $-NO_2$;
x is sulfur
n is 1 or 2;
R is 2. A compound according to claim 1 wherein x is sulfur.

3. A compound according to claim 1 wherein n is 1.

4. A compound according to claim 3 wherein T is hydrogen, chloro, bromo or ethoxy.

5. A compound according to claim 2 wherein R is

6. A compound according to claim 2 wherein R is

7. A compound according to claim 2 wherein R is

[pyridin-2-yl structure]

8. A method of regulating the natural growth and development of leguminous plants which method comprises applying to said leguminous plants or their habitat an effective plant growth regulating amount of a compound of the formula

[benzothiazolinone structure with T(n), X, C=O, N-CH2R]

wherein:
T is hydrogen, $C_{1-5}$ alkyl, halo, —$CF_3$, —CN or —$NO_2$;
x is sulfur
n is 1 or 2;
R is

[three pyridyl structures: 2-, 3-, and 4-pyridyl]

9. A method according to claim 9 wherein x is sulfur.
10. A method according to claim 8 wherein n is 1.
11. A method according to claim 10 wherein T is hydrogen, chloro, bromo, or ethoxy.
12. A method according to claim 9 wherein R is

[pyridyl structure]

13. A method according to claim 9 wherein R is

[pyridyl structure]

14. A method according to claim 9 wherein R is

[pyridyl structure]

15. A plant growth regulating composition comprising inert adjuvant and as the active ingredient, from about 5 to about 95 parts by weight of a compound of the formula

[benzothiazolinone structure with T(n), X, C=O, N-CH2R]

wherein:
T is hydrogen, $C_{1-5}$ alkyl, halo, —$CF_3$, —CN or —$NO_2$;
x is sulfur
n is 1 or 2;
R is

[three pyridyl structures: 2-, 3-, and 4-pyridyl]

16. A composition according to claim 15 wherein x is sulfur.
17. A composition according to claim 15 wherein n is 1.
18. A composition according to claim 17 wherein T is hydrogen, chloro, bromo or ethoxy.
19. A composition according to claim 16 wherein R is

[pyridyl structure]

20. A composition according to claim 16 wherein R is

[pyridyl structure]

21. A composition according to claim 16 wherein R is

[pyridyl structure]

* * * * *